United States Patent [19]

Parran, Jr. et al.

[11] Patent Number: 4,515,772

[45] Date of Patent: May 7, 1985

[54] ORAL COMPOSITIONS

[75] Inventors: John J. Parran, Jr., Cincinnati; Nabil Y. Sakkab, Loveland, both of Ohio

[73] Assignee: The Procter & Gamble Company, Cincinnati, Ohio

[21] Appl. No.: 591,228

[22] Filed: Mar. 19, 1984

Related U.S. Application Data

[63] Continuation of Ser. No. 391,040, Jun. 22, 1982, abandoned.

[51] Int. Cl.$^3$ ............................................. A61K 7/16
[52] U.S. Cl. ........................................ 424/57; 424/49
[58] Field of Search ................................... 424/49–58

[56] References Cited

U.S. PATENT DOCUMENTS

| | | | |
|---|---|---|---|
| 2,772,203 | 11/1956 | Salzmann | 424/54 |
| 2,941,926 | 6/1960 | Salzmann et al. | 424/57 |
| 3,137,632 | 6/1964 | Schiraldi | 424/49 |
| 3,431,339 | 3/1969 | Gyarmathy et al. | 424/57 |
| 3,737,522 | 6/1973 | Francis | 424/54 |
| 3,927,201 | 12/1975 | Baines et al. | 424/54 |
| 3,927,202 | 12/1975 | Harvey et al. | 424/57 |
| 4,002,732 | 1/1977 | Gault | 424/49 |
| 4,041,149 | 8/1977 | Gaffar et al. | 424/57 |
| 4,066,745 | 1/1978 | Tomlinson et al. | 424/49 |
| 4,069,311 | 1/1978 | Mannara | 424/49 |
| 4,071,614 | 1/1978 | Grimm | 424/58 |
| 4,075,316 | 2/1978 | Cordon | 424/57 |
| 4,089,943 | 5/1978 | Roberts et al. | 424/49 |
| 4,130,636 | 12/1978 | Tomlinson | 424/57 |
| 4,132,772 | 1/1979 | Barth et al. | 424/54 |
| 4,174,387 | 11/1979 | Cordon et al. | 424/49 |
| 4,235,874 | 11/1980 | Norfleet | 424/52 |
| 4,241,049 | 12/1980 | Colodney et al. | 424/54 |
| 4,244,931 | 1/1981 | Jarvis et al. | 423/266 |
| 4,247,526 | 1/1981 | Jervis et al. | 423/266 |
| 4,264,580 | 4/1981 | Barberio | 424/57 |
| 4,296,096 | 10/1981 | Pierce | 424/152 |
| 4,301,143 | 11/1981 | Barberio | 424/57 |
| 4,309,409 | 1/1982 | Coll-Palagos et al. | 424/57 |
| 4,314,990 | 2/1982 | Denny et al. | 424/57 |
| 4,323,551 | 4/1982 | Parran, Jr. | 424/54 |
| 4,340,583 | 7/1982 | Wason | 424/57 |
| 4,348,382 | 9/1982 | Pierce et al. | 424/57 |
| 4,356,168 | 10/1982 | Harvey et al. | 424/52 |
| 4,357,317 | 11/1982 | Wein et al. | 424/57 |

FOREIGN PATENT DOCUMENTS 4945 4/1974 Japan .

OTHER PUBLICATIONS

Draus, F. J. et al., "Pyrophosphate and Hexametaphosphate Effects in In-Vitro Calculus Formation", *Arch. Oral Biol.* (15), pp. 893–896, 1970.

*Primary Examiner*—Shep K. Rose
*Attorney, Agent, or Firm*—Richard C. Witte; John V. Gorman; Douglas C. Mohl

[57] ABSTRACT

Disclosed are oral compositions containing particular pyrophosphate salts which provide an anticalculus benefit.

8 Claims, No Drawings

ORAL COMPOSITIONS

This application is a continuation, of application Ser. No. 391,040, filed June 22, 1982, now abandoned.

TECHNICAL FIELD

The present invention relates to oral compositions, liquid dentifrices, toothpastes and mouthwashes, which provide an anticalculus benefit.

BACKGROUND OF THE INVENTION

Dental calculus, or tartar as it is sometimes called, is a deposit which forms on the surfaces of the teeth at the gingival margin. Supragingival calculus appears principally in the areas near the orifices of the salivary ducts; e.g., on the lingual surfaces of the lower anterior teeth and on the buccal surfaces of the upper first and second mclars, and on the distal surfaces of the posterior molars.

Mature calculus consists of an inorganic portion which is largely calcium phosphate arranged in a hydroxyapatite crystal lattice structure similar to bone, enamel and dentine. An organic portion is also present and consists of desquamated epithelial cells, leukocytes, salivary sediment, food debris and various types of microorganisms.

As the mature calculus develops, it becomes visibly white or yellowish in color unless stained or discolored by some extraneous agent. In addition to being unsightly and undesirable from an aesthetic standpoint, the mature calculus deposits are constant sources of irritation of the gingiva.

A wide variety of chemical and biological agents have been suggested in the art to retard calculus formation or to remove calculus after it is formed. Mechanical removal of this material periodically by the dentist is, of course, routine dental office procedure.

The chemical approach to calculus inhibition generally involves chelation of calcium ion and/or crystal growth inhibition which prevents the calculus from forming and/or breaks down mature calculus by removing calcium.

The prior art discloses a number of chelating agents for this purpose. British Patent No. 490,384, Feb. 15, 1937, discloses oral compositions containing ethylenediaminetetraacetic acid, nitrilotriacetic acid and related compounds as anticalculus agents. U.S. Pat. No. 3,678,154, July 18, 1972 to Widder et al discloses oral compositions containing certain polyphosphonates and fluoride. U.S. Pat. No. 3,737,533, June 5, 1973 to Francis discloses oral compositions containing certain carbonyl diphosphonates.

In addition to the above references, the prior art discloses dentifrices and mouthwashes containing soluble pyrophosphate salts which have been indicated for a variety of purposes. Included among such references are U.S. Pat. No. 2,941,926, June 21, 1960 to Salzmann et al which discloses dental powders containing chlorophyll and pyrophosphate salts. U.S. Pat. No. 3,137,632, June 16, 1964 to Schiraldi discloses toothpastes containing pyrophosphate salts. U.S. Pat. Nos. 3,927,201 and 3,297,202, Dec. 16, 1975 to Baines et al and Harvey et al, respectively, discloses toothpastes which utilize soluble pyrophosphates as abrasives. U.S. Pat. No. 4,244,931, Jan. 13, 1981 and U.S. Pat. No. 4,247,526, Jan. 27, 1981 to Jarvis et al disclose pyrophosphate salts in dicalcium phosphate systems. Jap. Patent Application Disclosure No. 4945-1974 discloses soluble pyrophosphates in a variety of dentifrice systems. U.S. Pat. No. 4,333,551, Apr. 6, 1982 to Parran discloses tetraalkali metal salts in mouthwash compositions. Finally Draus, Lesniewski and Miklos, *Pyrophosphate and Hexametaphosphate Effects In Vitro Calculus Formation*, Arch. Oral Biol., Vol. 15, pp. 893-896, (1970) disclose the in vitro effectiveness of soluble pyrophosphate salts against calculus. However, they indicate that pyrophosphate would be inhibitied by pyrophosphatase in vivo.

In spite of the many disclosures in the anticalculus and pyrophosphate areas, the need for an effective anticalculus product still exists. Surprisingly mixtures of certain pyrophosphate salts can provide a safe and effective product while also not presenting difficult formulation problems.

It is an object of the present invention to provide compositions which deliver an effective anticalculus benefit.

It is a further object of the present invention to provide an effective anticalculus product utilizing a mixture of soluble pyrophosphate salts.

It is still a further object of the present invention to provide an effective method for treating calculus.

These and other objects will beome more clear from the detailed description which follows.

All percentages and ratios used herein are by weight unless otherwise specified.

SUMMARY OF THE INVENTION

The present invention embraces an oral composition in the form of a mouthwash, liquid dentifrice or toothpaste comprising:

(a) from about 0% to about 70% of a dental abrasive selected from the group consisting silica, alumina, calcium pyrophosphate, insoluble metaphosphates and thermosetting polymerized resins;

(b) an amount of a fluoride source sufficient to supply from about 50 ppm to 3500 ppm of fluoride ions;

(c) an amount of a soluble pyrophosphate salt selected from the group consisting of dialkali metal and mixtures of dialkali metal and tetraalkali metal pyrophosphate salts sufficient to provide at least about 1.5% $P_2O_7^{-4}$; and (d) from about 2% to about 95% water wherein the pH of said composition is from about 6.0 to about 10.0 and the composition does not contain more than about 4.0 $K_4P_2O_7$.

The present invention also encompasses a method for retarding the development of dental calculus.

DETAILED DESCRIPTION OF THE INVENTION

The essential as well as optional components of the compositions of the present invention are described in the following paragraphs:

Dental Abrasive

The abrasives useful in the dentifrice composition aspect of the present invention include many different materials. Calcium pyrophosphate, including the β-phase calcium pyrophosphate prepared in accordance with the teaching of Schweizer, U.S. Pat. No. 3,112,247, Nov. 26, 1963, can be used. The β-phase calcium pyrophosphate is prepared by heating γ-phase calcium pyrophosphate to 700°-900° C. to change at least 50% of the γ-phase to β-phase and then immediately cooling. Another class of abrasives for use herein are the particulate thermosetting polymerized resins as described by Cooley et al in U.S. Pat. No. 3,070,510, Dec. 25, 1962. Suitable resins include, for example, melamines, phenolics, ureas, melamine-ureas, melamineformaldehydes, urea-formaldehydes, melamine-urea-formaldehydes, cross-linked epoxides, and cross-linked polyesters.

Silica dental abrasives are also useful in the present compositions. The silica abrasive polishing material generally has an average particle size ranging between about 0.1 to 30 microns, preferably 5 and 15 microns. The abrasive can be precipitated silica or silica gels such as the silica xerogels described in Pader et al; U.S. Pat. No. 3,538,230; issued Mar. 2, 1970 and incorporated herein by reference. Preferred are the silica xerogels marketed under the tradename "Syloid" by the W. R. Grace & Company, Davison Chemical Division. Also preferred are the precipitated silica materials such as those marketed by the J. M. Huber Corporation under the tradename, "Zeodent". The types of silica dental abrasives useful in the toothpastes of the present invention are described in more detail in DiGiulio, U.S. Pat. No. 3,862,307; issued Jan. 21, 1975, incorporated herein by reference.

Other suitable abrasives include alumina, and the insoluble metaphosphates such as insoluble sodium metaphosphate (IMP). Mixtures of abrasives can also be used. In any case, the total amount of abrasive in the dentifrice embodiments of this invention can range from 0% to 70% by weight of the dentifrice. Preferably, toothpastes contain from 10% to 50% by weight of abrasive.

The preferred abrasives are the $\beta$-phase calcium pyrophosphate of U.S. Pat. No. 3,112,247; alumina insoluble metaphosphate; the resinous abrasives of U.S. Pat. No. 3,070,510; and the silica abrasives since they are more compatible with the agents. Most preferred are the silica abrasives.

Fluoride Ion Source

The second essential component of the compositions herein is a fluoride ion source. The number of such sources is great and includes those disclosed in U.S. Pat. No. 3,535,421, Oct. 20, 1970 to Briner et al, incorporated herein by reference. Typical materials include:

Stannous fluoride, potassium fluoride, lithium fluoride, cesium fluoride, ammonium fluoride, aluminum fluoride, cupric fluoride, indium fluoride, stannous fluorozirconate, lead fluoride, ferric fluoride, nickel fluoride, paladium fluoride, silver fluoride, zinc fluoride, zirconium fluoride, hexylamine hydrofluoride, laurylamine hydrofluoride, myristylamine hydrofluoride, decanolamine hydrofluoride, octadecenylamine hydrofluoride, myristoxyamine, hydrofluoride, diethylaminoethyloctoylamide hydrofluoride, diethanolamineoethyloleylamide hydrofluoride, diethanolaminopropyl-N'-octadecenylamine dihydrofluoride, 1-ethanol-2-hexadecylimidazoline dihydrofluoride, octoylethanolamine hydrofluoride, octyltrimethylammonium fluoride, dodecylethyldimethylammonium fluoride, tetraethylammonium fluoride, dilauryldimethylammonium fluoride. $\Delta^{8,9}$-octadecenylbenzyldimethylammonium fluoride, dioctyldiethylammonium fluoride, cyclohexylcetyldimethylammonium fluoride, furfuryllauryldimethylammonium fluoride, phenoxyethylcetyldimethylammonium fluoride, N:N'-tetramethyl-N:N;-dilaurylethylenediammonium difluoride, N-cetylpyridinium fluoride, N:N-dilauryl-morpholinium fluoride, N-myristyl-N-ethylmorpholinium fluoride, N-(octylaminocarbonylethyl)-N-benzyl-dimethylammonium fluoride, N($\beta$-hydroxydodecyl) trimethylammonium fluoride, N-phenyl-N-hexadecyldiethylammonium fluoride, N-cyclohexyl-N-octadecyldimethylammonium fluoride, N-(2-carbomethoxyethyl)-N-benzyldimethylammonium fluoride, N-(2-carbocyclohexoxyethyl)-N-myristyldimethylammonium fluoride, N-(2-carbobenzyloxyethyl)-N-dodecyldimethylammonium fluoride, N-[2-(N:N'-dimethylaminocarbonyl)-ethyl]-N-dodecyldiethylammonium fluoride, N-carboxymethyl-N-cicosyldimethylammonium fluoride, betaine hydrofluoride, sarcosine stannous fluoride, alanine stannous fluoride, glycine potassium fluoride, sarcosine potassium fluoride, glycine hydrofluoride, lysine hydrofluoride, alanine hydrofluoride, betaine zirconium fluoride, sodium monofluoro phosphate and mixtures thereof. Sodium fluoride is the preferred fluoride source.

The amount of the fluoride ion source should be sufficient to provide from about 50 ppm to 3500 ppm, preferably from about 500 ppm to 3000 ppm of fluoride ions.

Di alkali Metal and Tetra alkali Metal Salts

The pyrophosphate salts useful in the present compositions include dialkali metal pyrophosphate and mixtures of the dialkali metal and tetraalkali metal pyrophosphate salts. $Na_2H_2P_2O_7$, $Na_4P_2O_7$ and $K_4P_2O_7$ in their unhydrated as well as hydrated forms are the preferred species. The levels of each of these species which preferably are used in the compositions are as follows (all are in the unhydrated form).

| | | |
|---|---|---|
| $Na_2H_2P_2O_7$ | 0.5% | 13.8% |
| $Na_4P_2O_7$ | 0 | 6.0% |
| $K_4P_2O_7$ | 0 | 4.0% |

The minimum amount of $P_2O_7^{-4}$ required in the present compositions, 1.5% can therefore be provided solely by $Na_2H_2P_2O_7$ or mixtures of $Na_2H_2P_2O_7$ with either or both of the tetra alkali metal salts. Preferred are binary mixtures of the sodium salts and ternary mixtures of those with the tetra potassium salt. The upper limits on the sodium species are determined by solubility considerations while the tetra potassium level is established for taste reasons.

The pyrophosphate salts are described in more detail in Kirk & Othmer, *Encyclopedia of Chemical Technology*, Second Edition, Volume 15, Interscience Publishers (1968) incorporated herein by reference.

Water

Water is another essential component of the compositions of this invention. Water employed in the preparation of commercially suitable oral compositions should preferably be of low ion content and free of organic impurities. Water comprises from about 2% to about 95%, preferably from about 20% to about 95% of the compositions of this invention. When in the form of toothpastes, the amount of water is preferably from about 2% to about 45%, while mouthwashes preferably contain from about 45% to about 95%.

Optional Components

In addition to the above described essential components, the oral compositions of this invention can contain a variety of optional conventional oral composition components. Such optional ingredients include sudsing agents, flavoring agents, sweetening agents, antiplaque agents, coloring agents, and pigments.

A preferred optional ingredient is a sudsing agent. Suitable sudsing agents are those which are reasonably stable and form suds throughout a wide pH range, i.e., non-soap anionic, nonionic, cationic, zwitterionic and amphoteric organic synthetic detergents. Sudsing agents of these types are described more fully in Agricola et al; U.S. Pat. No. 3,959,458; issued May 25, 1976 and in Haefele; U.S. Pat. No. 3,937,807; issued Feb. 10, 1976. Both of these patents are incorporated herein by reference.

Anionic sudsing agents useful herein include the water-soluble salts of alkyl sulfates having from 10 to 18 carbon atoms in the alkyl radical and the water-soluble salts of sulfonated monoglycerides of fatty acids having from 10 to 18 carbon atoms. Sodium lauryl sulfate and sodium coconut monoglyceride sulfonates are examples of anionic surfactants of this type. Mixtures of anionic surfactants can also be employed.

The nonionic sudsing agents which can be used in the compositions of the present invention can be broadly defined as compounds produced by the condensation of alkylene oxide groups (hydrophilic in nature) with an organic hydrophobic compound which may be aliphatic or alkylaromatic in nature. Examples of suitable nonionic sudsing agents include the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

The zwitterionic synthetic sudsing agents useful in the compositions of the present invention can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, orphosphonate.

The cationic sudsing agents useful in the compositions of the present invention can be broadly defined as quaternary ammonium compounds having one long alkyl chain containing from about 8 to about 18 carbon atoms such as lauryl trimethylammonium chloride; cetyl pyridinium chloride, cetyl trimethylammonium bromide; di-isobutylphenoxyethoxyethyl-dimethylbenzylammonium chloride; coconutalkyltrimethylammonium nitrite; cetyl pyridinium fluoride; etc.

The amphoteric sudsing agents useful in the present invention can be broadly described as derivatives of aliphatic secondary and tertiary amines in which the aliphatic radical can be straight chain or branched and wherein one of the aliphatic substituents contains from about 8 to about 18 carbon atoms and one contains an anionic water-solubilizing group, e.g., carboxylate, sulfonate, sulfate, phosphate, or phosphonate.

The sudsing agent can be present in the compositions of this invention in an amount from about 0% to about 10% by weight of the total composition.

Flavoring agents can also be added to the instant compositions. Suitable flavoring agents include oil of wintergreen, oil of peppermint, oil of spearmint, oil of sassafras, and oil of clove. Sweetening agents which can be used include saccharin, dextrose, levulose, aspartame, D-tryptophan, dihydrochalcones, acesulfame and sodium cyclamate. Flavoring agents are generally used in the compositions at levels of from about 0.4% to about 2% by weight and sweetening agents at levels of from about 0.1% to about 5% by weight.

Binders can also be used with the toothpastes of of the present inventions. Such binders include, for example, xanthan gum, carrageenan (Irish moss, Viscarin ®), and carboxyvinyl polymers. These binders are generally present at a level of from about 0.1% to 1%.

Bis-biguanide antiplaque agents can also optionally be added to the compositions of this invention. Such agents include chlorhexidine (1,6-bis [$N^5$-p-chlorophenyl-$N^1$-biguanido]hexane), the soluble and insoluble salts thereof and related materials such as 1,2-bis($N^5$-p-trifluoromethylphenyl-$N^1$-biguanido)ethane are described more fully in Haefele, U.S. Pat. No. 3,923,002, issued Jan. 20, 1976; Haefele, U.S. Pat. No. 3,937,807, issued Feb. 10, 1976; Procter & Gamble, Belgian Pat. No. 843,244, published Dec. 22, 1976 and Procter & Gamble, Belgian Pat. No. 844,764, published Jan. 31, 1977. These patents are incorporated herein by reference.

If present, the optional antiplaque agents generally comprise from about 0% to about 5% by weight of the compositions herein.

Another optional component of the compositions herein is a humectant. The humectant serves to keep the toothpaste compositions from hardening upon exposure to air and in mouthwashes give a moist feel to the mouth. Certain humectants can also impart desirable sweetness of flavor to mouthwash and toothpaste compositions. The humectant, on a pure humectant basis, generally comprises from about 0% to 70%, preferably from about 0% to 55%, by weight of the compositions herein.

Suitable humectabts for use in this invention include edible polyhydric alcohols such as glycerine, sorbitol, xylitol and propylene glycol. Sorbitol is frequently employed as a 70% aqueous solution known as Sorbo ®.

The mouthwashes herein may also contain ethanol in an amount of from about 0 to about 30%.

The pH of the compositions herein is in the range of 6.0 to 10.0, preferably from 7.3 to 9.0. The pH is preferably achieved through a proper balancing of the pyrophosphate salts or by the addition of an alkaline or acidic agent.

Method of Manufacture

The compositions herein are made using conventional mixing techniques. A typical method is described in Example I.

Industrial Applicability

The compositions of the present invention are used in a conventional manner.

The following examples further describe and demonstrate preferred embodiments within the scope of the present invention. The examples are given solely for the purpose of illustration and are not to be construed as limitations of this invention. Many variations thereof are possible without departing from the invention's spirit and scope.

EXAMPLE I

The following is a toothpaste representative of the present invention.

| Component | % |
| --- | --- |
| Distilled Water | 16.484 |
| Sorbitol (70% Aqueous Solution) | 49.563 |
| Sodium Saccharin | 0.300 |
| Dye Solution | 0.350 |
| Precipitated Silica | 20.00 |
| Sodium Fluoride | 0.243 |
| Flavor | 1.330 |
| Sodium Alkyl Sulfate (27.9% Aqueous Solution) | 5.000 |
| Carbopol 940s* | 0.180 |
| Xanthan Gum | 0.600 |
| $Na_4P_2O_7$ | 2.400 |
| $Na_2H_2P_2O_7$ | 1.190 |
| $K_4P_2O_7$ (63.5% Aqueous Solution) | 2.360 |
| | 100.000% |

*A carboxy vinyl polymer offered by B. F. Goodrich Company.

The above composition was made by combining the water and part of the sorbitol in an agitated mixture and heating this mixture to 140° F. The $Na_2H_2P_2O_7$, $Na_4P_2O_7$, saccharin, sodium fluoride and precipitated silica were then added in order and the total mixture was mixed for from 5 to 10 minutes. The flavor, dye and surfactant were then added. In a separate vessel the remainder of the sorbitol, the Carbopol and the xanthan gum were slurried together and then added to the main mix tank. The complete batch was mixed for about one-half hour and subsequently milled and deaerated.

EXAMPLE II

The following is another representative toothpaste of the present invention.

| Component | % |
| --- | --- |
| Sorbitol (70% Aqueous Solution) | 50.743 |
| Distilled Water | 16.484 |
| Sodium Saccharin | 0.300 |
| Dye Solution | 0.350 |
| Precipitated Silica | 20.000 |
| Sodium Fluoride | 0.243 |
| Flavor | 1.330 |
| Sodium Alkyl Sulfate (27.9% Aqueous Solution) | 5.000 |
| Carbopol 940S | 0.180 |
| Xanthan Gum | 0.600 |
| $Na_4P_2O_7$ | 3.400 |
| $Na_2H_2P_2O_7$ | 1.370 |

| Component | % |
| --- | --- |
| | 100.000% |

Both the composition of Example I and that of Example II are effective in reducing calculus and possess acceptable cosmetic properties.

In addition to the levels and combinations of ingredients shown in these examples, others can be used which are consistent with the invention disclosed and claimed herein.

What is claimed is:

1. An oral composition in the form of a toothpaste comprising:
   (a) from about 10% to about 70%, of a dental abrasive selected from the group consisting of insoluble metaphosphates, alumina, thermosetting polymerized resins and silica;
   (b) an amount of a fluoride ion source sufficient to supply from about 50 ppm to about 3500 ppm of fluoride ions;
   (c) an amount of a pyrophosphate salt selected from the group consisting of dialkali metal and mixtures of dialkali metal and tetraalkali metal pyrophosphate salts sufficient to provide at least 1.5% $P_2O_7^{-4}$.
   (d) the remainder water; wherein the pH of said composition is from about 6.0 to about 10.0 and the composition does not contain more than about 4.0% $K_4P_2O_7$.

2. An oral composition according to claim 1 wherein the abrasive is a silica dental abrasive.

3. An oral composition according to claim 2 wherein sodium fluoride is the fluoride ion source.

4. An oral composition according to claim 3 wherein the pyrophosphate ion is provided by a mixture of disodium pyrophosphate and tetra sodium pyrophosphate.

5. An oral composition according to claim 3 wherein the pyrophosphate ion is provided by a mixture of disodium pyrophosphate, tetrasodium pyrophosphate and tetrapotassium pyrophosphate.

6. An oral composition according to claim 3 which in addition contains from 0 to about 10% of a sudsing agent.

7. An oral composition according to claim 3 which in addition contains from about 0.1% to about 10% of a binder.

8. An oral composition according to claim 3 which in addition contains from 0 to about 70% of a humectant.

* * * * *